(12) United States Patent
Suzuki

(10) Patent No.: US 7,331,784 B2
(45) Date of Patent: Feb. 19, 2008

(54) MOUTHPIECE

(75) Inventor: Shuhei Suzuki, Tokyo (JP)

(73) Assignee: Futek, Inc., Tokyo (JP)

( * ) Notice: Subject to any disclaimer, the term of this patent is extended or adjusted under 35 U.S.C. 154(b) by 0 days.

(21) Appl. No.: 11/394,116

(22) Filed: Mar. 31, 2006

(65) Prior Publication Data

US 2006/0172252 A1    Aug. 3, 2006

Related U.S. Application Data

(63) Continuation-in-part of application No. 10/944,740, filed on Sep. 21, 2004, now abandoned.

(30) Foreign Application Priority Data

Jun. 1, 2004    (JP)    .............................. 2004-162835

(51) Int. Cl.
*A61C 3/00*    (2006.01)

(52) U.S. Cl. .......................................... 433/29; 433/37

(58) Field of Classification Search ................ 433/29, 433/37, 215, 216
See application file for complete search history.

(56) References Cited

U.S. PATENT DOCUMENTS

| | | | |
|---|---|---|---|
| 6,416,319 | B1 | 7/2002 | Cipolla |
| 6,616,447 | B1 | 9/2003 | Rizoiu et al. |
| 2003/0125782 | A1* | 7/2003 | Streeter ........................ 607/88 |
| 2004/0193235 | A1 | 9/2004 | Altshuler et al. |
| 2005/0048444 | A1 | 3/2005 | Creamer |
| 2005/0074723 | A1* | 4/2005 | Ostler et al. ................. 433/216 |

* cited by examiner

*Primary Examiner*—Melba Bumgarner
(74) *Attorney, Agent, or Firm*—Wenderoth, Lind & Ponack, L.L.P.

(57) ABSTRACT

A mouthpiece of the present invention includes a light irradiation section for irradiating the front surfaces of teeth with light having a predetermined wavelength, and the light irradiation section has a blue light emitting diode or an ultraviolet light emitting diode. The mouthpiece is to be attached to the teeth, and the front teeth are irradiated with a blue light or ultraviolet light emitted by the light emitting diode, thereby performing teeth whitening processing.

16 Claims, 5 Drawing Sheets

MOUTHPIECE

This application is a continuation-in-part of U.S. application Ser. No. 10/944,740, filed Sep. 21, 2004, now abandoned.

BACKGROUND OF THE INVENTION

1. Field of the Invention

The present invention relates to a mouthpiece, and particularly relates to a mouthpiece that is suitable for performing a so-called whitening processing for whitening teeth.

2. Description of the Related Art

In general, as an apparatus that performs teeth whitening processing, one that is disclosed in Unexamined Japanese Patent Publication No. 2003-242806 is known. The conventional whitening processor irradiates teeth with ultraviolet rays using a halogen lamp to perform the teeth whitening processing.

However, in a method in which the teeth are irradiated with ultraviolet rays using a halogen lamp to perform the teeth whitening processing, since the ultraviolet rays emitted by the halogen lamp have high light intensity, there is difficulty in handling the ultraviolet rays. For example, when irradiation was continued for a long time, there was a possibility that the surfaces of the teeth and gums around the teeth would be damaged. Thus, a fixed skill was required for the ultraviolet irradiation, and the help of a specialist such as a dentist was needed. Accordingly, it has been demanded that whitening can be easily performed at home.

SUMMARY OF THE INVENTION

An object of the present invention is to provide a mouthpiece that can easily and safely perform teeth whitening processing at home.

The present invention is a mouthpiece including a light irradiation section that irradiates the front surfaces of teeth with light having a predetermined wavelength. The light irradiation section has a blue light emitting diode or ultraviolet light emitting diode, and a blue light or ultraviolet light is emitted by the light emitting diode.

According to the present invention, in the case where teeth whitening processing is performed, the mouthpiece is put in the mouth to irradiate the teeth with the blue light or ultraviolet light from the light emitting diode of the light irradiation section. In this way, since the teeth are irradiated with the blue light or ultraviolet light from the light emitting diode, the light intensity is small as compared with irradiation of the ultraviolet rays from a halogen lamp, and this brings about safety without the possibility that the surfaces of the teeth and the gums around the teeth will be damaged. Further, since handling is easy, teeth whitening processing can be easily performed at home. Moreover, since the blue light emitting diode or ultraviolet light emitting diode is attached to the mouthpiece, the mouthpiece is only put in the mouth to make it possible to easily perform whitening processing.

Furthermore, according to the present invention, the mouthpiece further includes a horseshoe main body attached to an oral cavity, and a belt-like flexible substrate embedded along the horseshoe shape of the main body. The light irradiation section is desirably attached to the flexible substrate. In this way, since the flexible substrate is embedded in the main body of the mouthpiece, the mouthpiece has high water resistance for the light emitting diode and can be washed with water.

Furthermore, according to the present invention, the flexible substrate desirably faces the front teeth when being attached to the oral cavity and multiple light emitting diodes are desirably provided in a longitudinal direction of the flexible substrate, and at least the entirety of the front teeth is desirably irradiated with the blue light or ultraviolet light. In this way, since the multiple light emitting diodes are provided in the longitudinal direction of the flexible substrate, the entirety of the front teeth can be irradiated with the blue light or ultraviolet light to eliminate the need for performing light irradiation for each tooth to make it possible to perform whitening processing effectively.

Still furthermore, according to the present invention, the light irradiation section desirably provides multiple irradiation times selectable by a switch. In this way, the user can select the preset irradiation time to make it possible to adjust irradiation time according to the individual's teeth state.

Also, the light irradiation section desirably emits the blue light or ultraviolet light with a blinking frequency of 1 kHz to 20 kHz. In particular, the light irradiation section emits blue or ultraviolet light by blinking at a rate (frequency) in a range of 1 kHz to 20 kHz. The reason why the frequency ranges 1 kHz to 20 kHz in this way is as follows. Namely, when the frequency is below 1 kHz, it is difficult to obtain a sufficient processing effect of whitening. While, when the frequency exceeds 20 kHz, it is difficult to obtain an effect proportional to the high frequency, resulting in wasting power consumption.

BRIEF DESCRIPTION OF THE DRAWINGS

These objects and other objects and advantages of the present invention will become more apparent upon reading of the following detailed description and the accompanying drawings in which.

DETAILED DESCRIPTION OF THE PREFERRED EMBODIMENT

Figure 1:
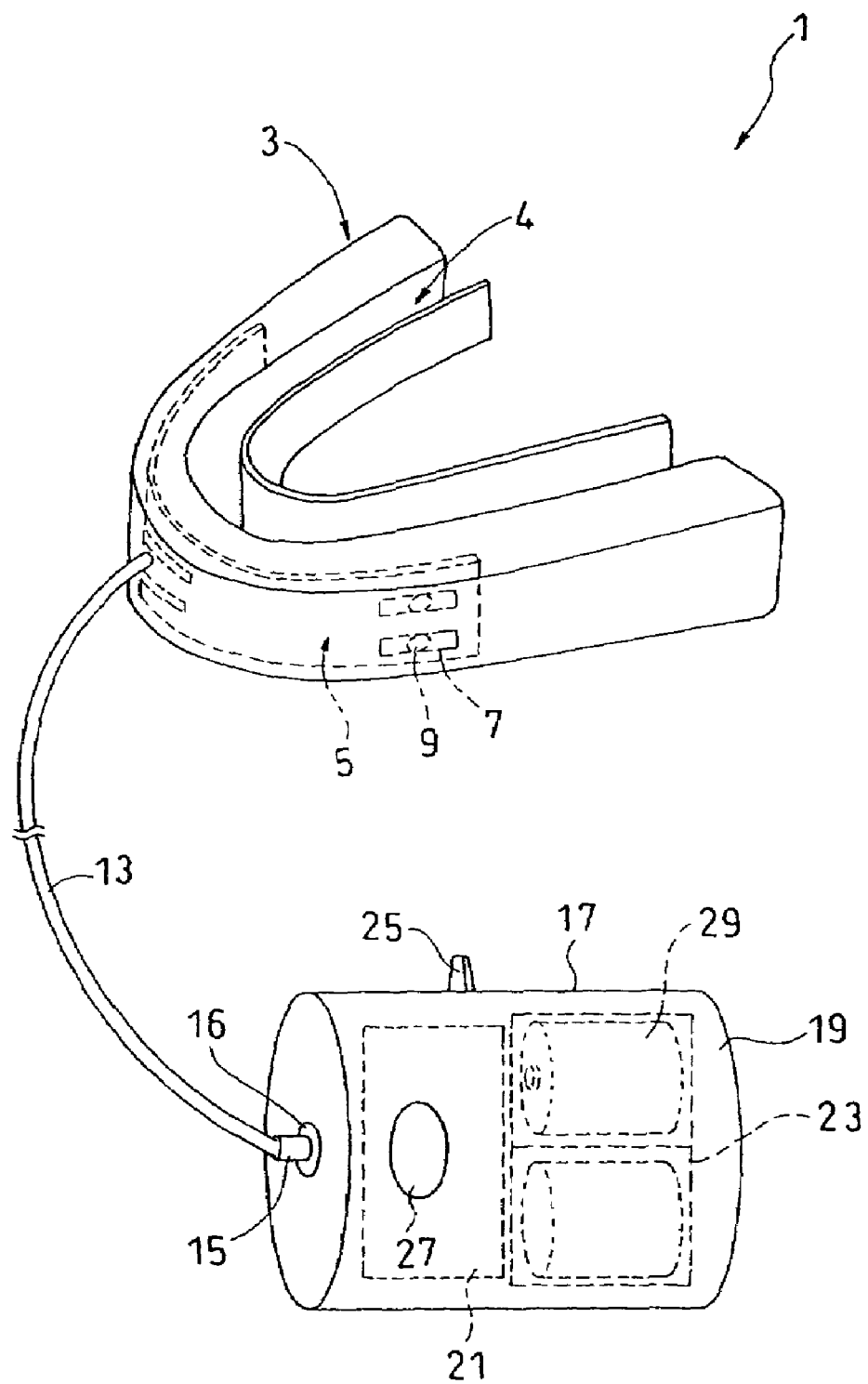
FIG. 1 is a perspective view illustrating a mouthpiece according to a first embodiment of the present invention.
Figure 2:
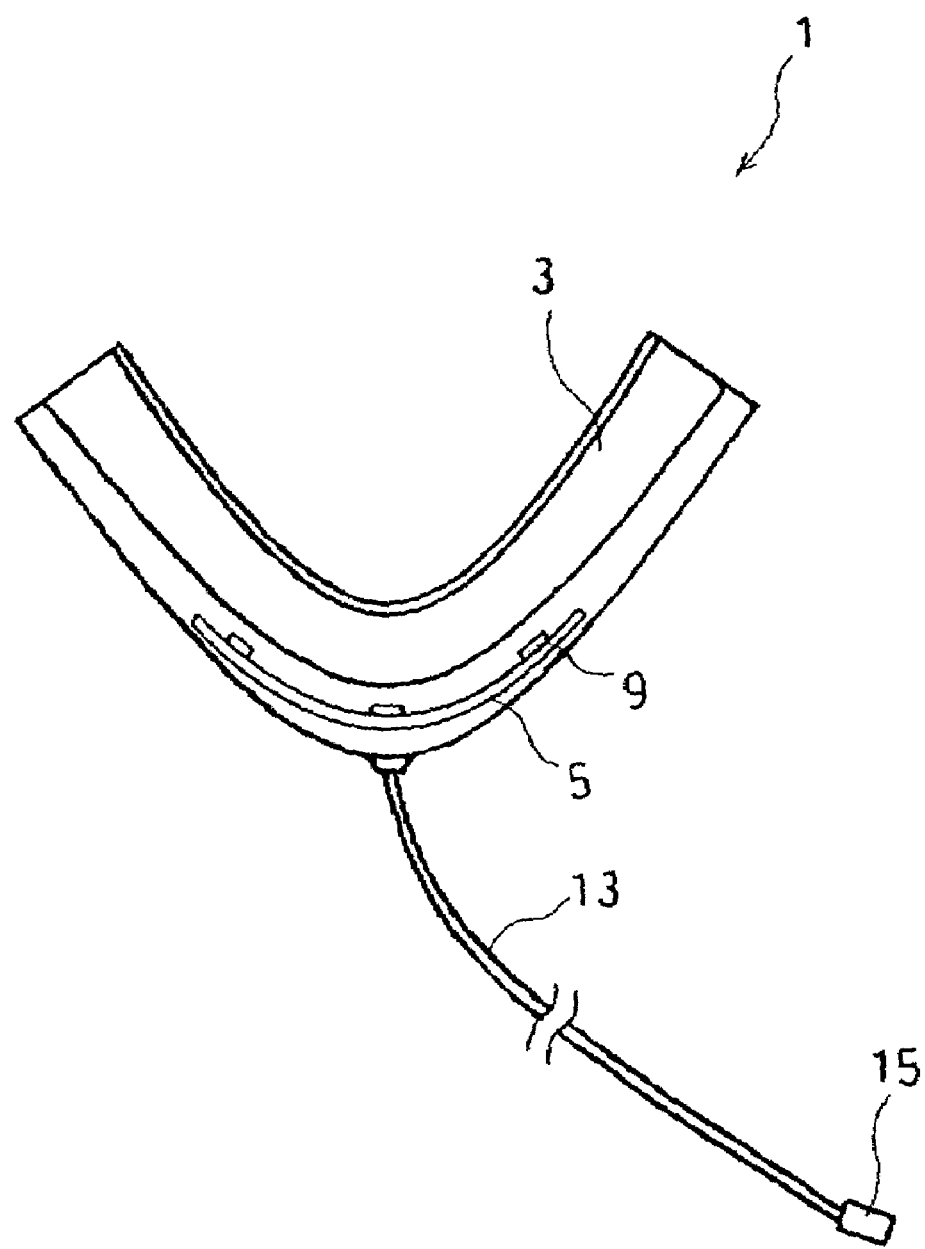
FIG. 2 is a plan view illustrating the mouthpiece shown in FIG. 1.
Figure 3:
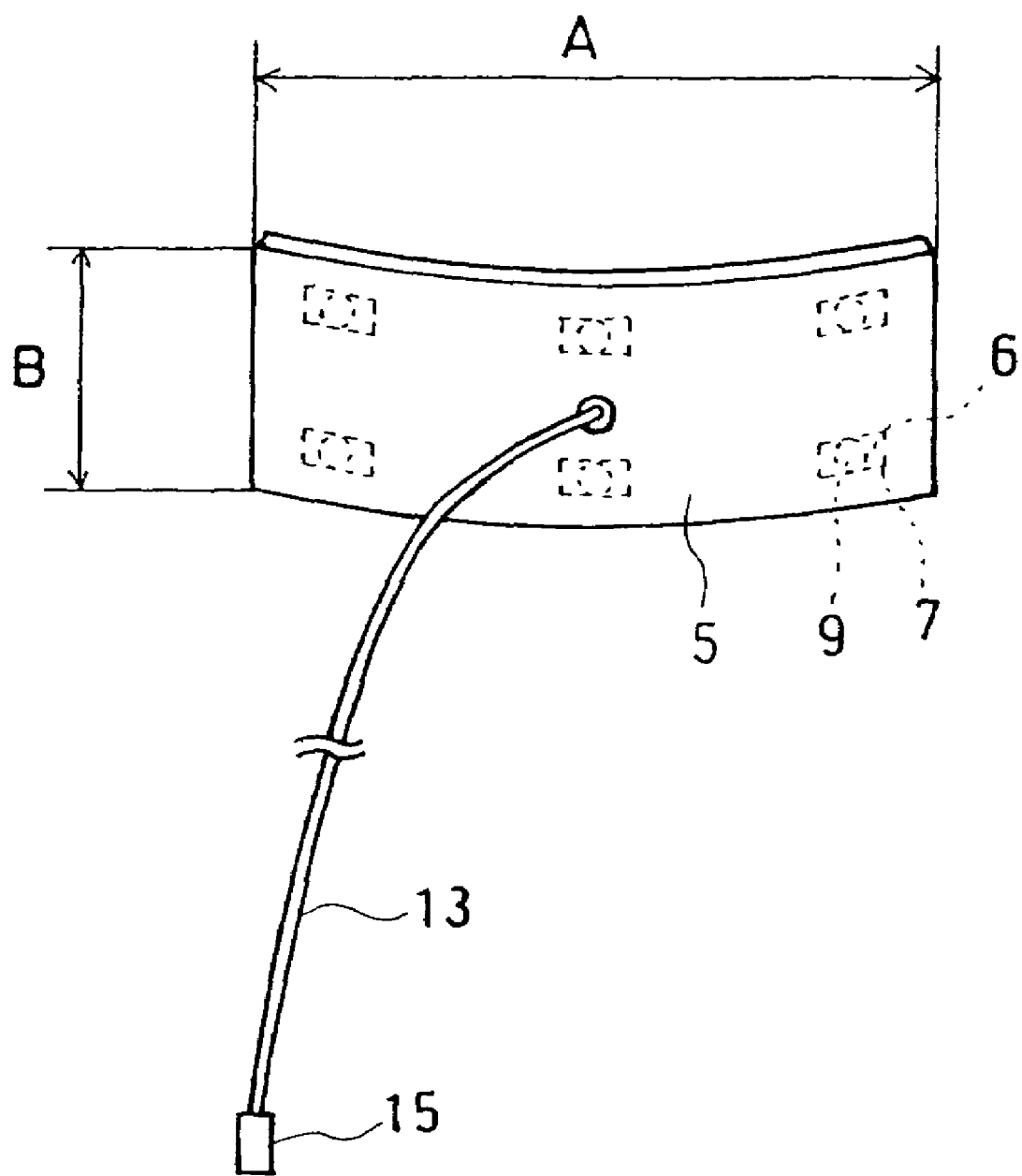
FIG. 3 is a perspective view illustrating an extracted flexible substrate shown in FIG. 1.
Figure 4:
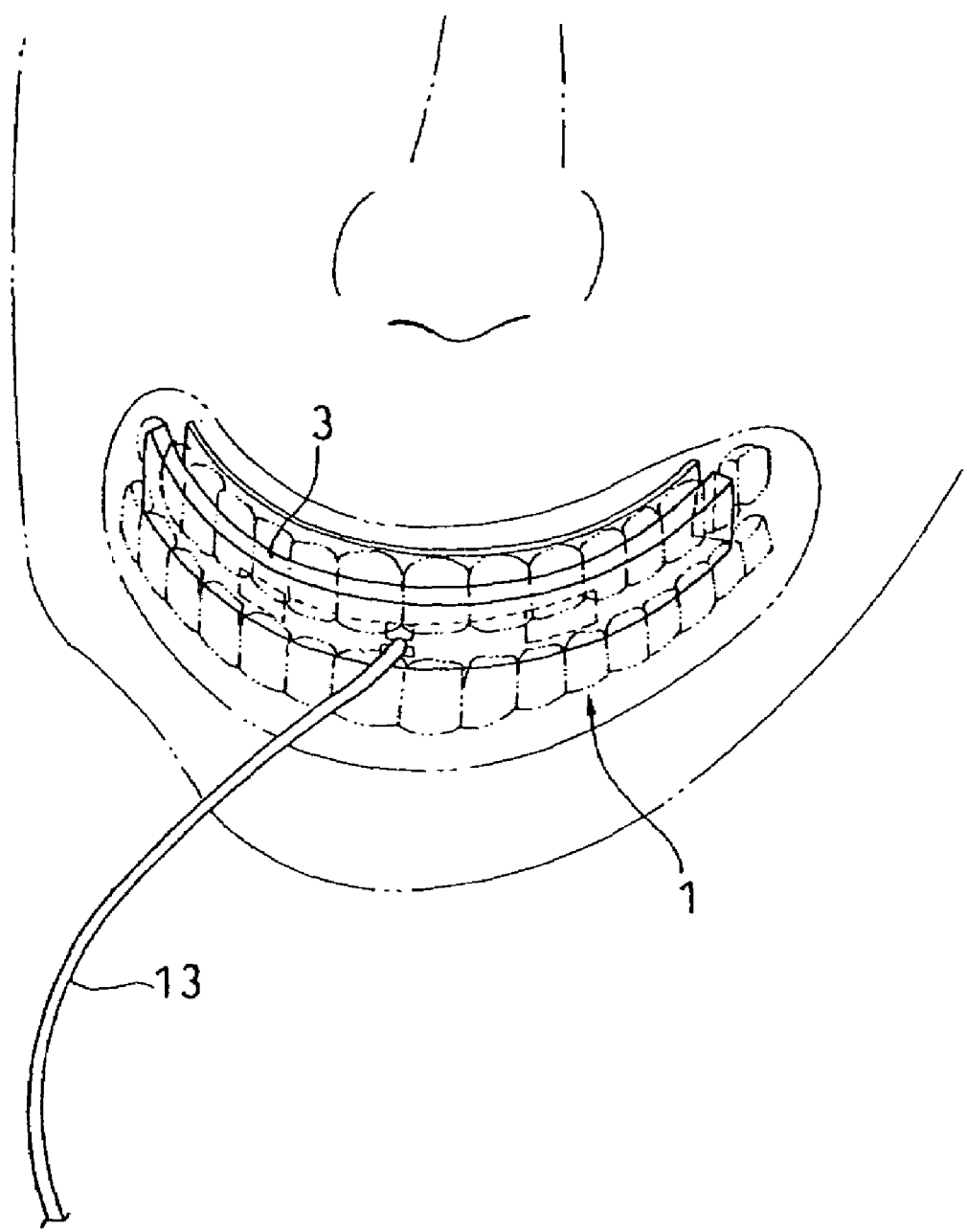
FIG. 4 is a schematic view illustrating a state in which the mouthpiece of FIG. 1 is used.

Embodiments of the present invention will be specifically explained with reference to the accompanying drawings. FIGS. 1 to 3 illustrate a first embodiment of the present invention.

A mouthpiece 1 according to a first embodiment includes a horseshoe-shaped main body 3 made of silicone resin attached to an oral cavity, a belt-like flexible substrate 5 embedded in the main body 3, an electronic cable 13 connected to the flexible substrate 5, and a controller 17 connected to an end portion of the electronic cable 13. The flexible substrate 5 has a light irradiation section 7 that irradiates the front surfaces of teeth with light having a predetermined wavelength.

The light irradiation section 7 includes a blue light emitting diode 9 for emitting light with a wavelength of about 450 nm. Two light irradiation sections 7 are provided at each of a substantially central portion and both ends in a longitudinal direction of the flexible substrate 5 (six in all).

Front teeth located at an upper side are irradiated with the light emitting diodes 9 attached to the upper side of the flexible substrate 5, and front teeth located at a lower side are irradiated with the light emitting diodes 9 attached to the lower side of the flexible substrate 5.

Moreover, a transparent plate 6 is attached to the light irradiation section 7 so as to be detachable, so that blue light from the light emitting diode 9 is transmitted therethrough to an external section. Furthermore, fine concave and convex portions are formed on a surface of the transparent plate 6 to scatter the blue light passing through the transparent plate 6.

Moreover, the light emitting diode 9 is controlled to provide irradiation with a frequency (i.e., blinking rate) of 1 kHz to 20 kHz. In other words, the light emitting diode 9 is controlled to emit light by blinking at a rate (i.e., a frequency) in a range of 1 kHz to 20 kHz. The reason why the frequency ranges 1 kHz to 20 kHz in this way is as follows. Namely, when the frequency is below 1 kHz, it is difficult to obtain a sufficient processing effect of whitening. While, when the frequency exceeds 20 kHz, it is difficult to obtain an effect proportional to the high frequency, resulting in wasting power consumption.

The flexible substrate 5 is made of polyimide and placed at a position facing at least the front teeth. The flexible substrate 5 is made of polyimide in this way to reduce an influence of heat at the time of embedding the flexible substrate 5 in the main body 5 of the mouthpiece 1 at a manufacturing time, making it possible to prevent the flexible substrate 5 from being deformed and damaged. In addition, the flexible substrate 5 has a length (FIG. 3 (A)) of 20 mm in a longitudinal direction and a length (FIG. 3 (B)) of 5 mm in a transverse direction.

A plug 15 is attached to an end portion of the electronic cable 13. The plug 15 is inserted into a jack 16 of the controller 17, so that the controller 17 and the flexible substrate 5 are electrically connected to each other. The electronic cable 13 has two cores and a length of about 1 m, and its surface is covered with a white silicone resin.

The controller 17 is cylindrically shaped with an elliptical section and is small enough to be held in one hand. A case 19 of the controller 17 is made of ABS (acrylonitrile-butadiene-styrene resin). Furthermore, the controller 17 includes a control substrate 21 that controls irradiation of the light emitting diode 9, a battery box 23 that contains batteries, a slide switch 25 that turns ON and OFF and sets irradiation time, and a start button 27 that starts light irradiation. In addition, two batteries 29 of 1.5V are contained in the battery box 23 and can be replaced with new ones when they are used up.

According to this embodiment, irradiation time can be selected from three levels by the slide switch 25, and any one of irradiation times: 10 minutes, 20 minutes, and 30 minutes can be selected.

An explanation will next be given of the function according to this embodiment. In the case where a user performs teeth whitening processing, the user puts the mouthpiece 1 in the user's mouth so that a groove 4 of the main body 3 is attached to the teeth. Then, the plug 15 of the electrical cable 13 is connected to the jack 16 of the controller 17. After that, the slide operation of the slide switch 25 is performed to turn on power and select any one of irradiation times: 10 minutes, 20 minutes, and 30 minutes. After that, when the start button 27 is pressed, light irradiation from the light irradiation section 7 is started, the front teeth are irradiated with blue light for the set irradiation time. In this way, the front surfaces of the front teeth are irradiated with blue light, making it possible to execute irradiation with a wavelength close to a wavelength region of light used for whitening processing.

Accordingly, since the teeth are irradiated with blue light emitted from the light emitting diode 9, light intensity is small as compared with irradiation of ultraviolet rays from the halogen lamp, and this brings about safety without the possibility that the surfaces of the teeth and the gums around the teeth will be damaged. Further, since the handling is easy, teeth whitening processing can be easily performed at home.

Since the blue light emitting diode 9 is attached to the mouthpiece 9, only the mouthpiece 1 is put in the mouth to make it possible to easily perform whitening processing.

Since the flexible substrate 5 is embedded in the main body 3 of the mouthpiece 1, the mouthpiece I has high water resistance for the light emitting diode 9 and can be washed with water after using the mouthpiece 1.

Figure 5:
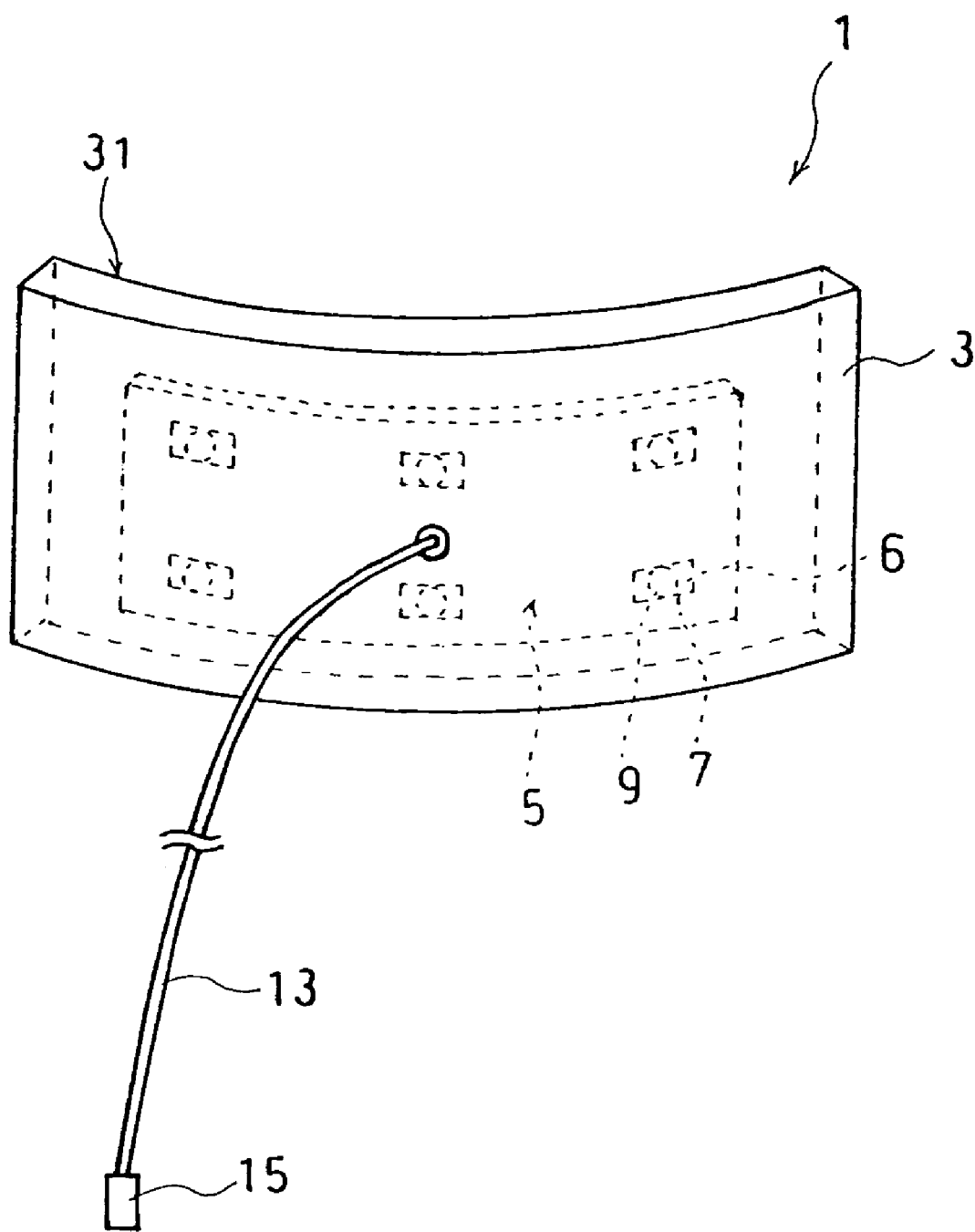
FIG. 5 is a perspective view illustrating a mouthpiece according to a second embodiment of the present invention.

Next, a second embodiment of the present invention will be explained with reference to FIG. 5. In the explanation given below, the same reference numerals as those of the first embodiment are added to the portions where the same function and effect are exerted as those of the first embodiment, and the explanation is omitted. The following mainly explains the points that are different from the first embodiment.

The mouthpiece 1 of the second embodiment is different from the first embodiment in the point that the main body 3 is formed like a belt instead of the horseshoe. In this case, as illustrated in FIG. 5, the flexible substrate 5 is embedded in the belt-like main body 3. In the case of performing the teeth whitening processing, a back surface portion 31 of the main body 3 is placed on the front surfaces of the front teeth. Then, the start button 27 of the controller 17 is pressed under this state to irradiate the front teeth with the blue light.

In this way, the main body 3 is band-shaped to make it possible to easily place it against the surfaces of the front teeth in the mouth and make the entirety of the apparatus compact.

The present invention is not limited to the above described embodiments, and various modifications may be possible without departing from the scope of the present invention.

The light emitting diodes are not limited to the blue light emitting diodes, and an ultraviolet light emitting diode with a wavelength of about 400 nm may be possible.

The number of light emitting diodes 9 is not limited to six, and any number may be possible.

In the aforementioned embodiments, through the irradiation time of light emitting diodes can be selected from three levels of 10 minutes, 20 minutes, and 30 minutes, the present invention is not limited to this, and, for example, two levels may be possible and four or more levels may also be possible. Moreover, the maximum irradiation time may be more than 30 minutes.

In the aforementioned embodiments, though both the flexible substrate 5 and the controller 17 are connected to each other by the electrical cable 13 to control light irradiation from the light emitting diodes 9, the present invention is not limited to this, and no electrical cable 13 may be provided. In this case, a control substrate, small-size batteries, and a start button are attached to the main body 3 of the mouthpiece 1, so that light irradiation from the light emitting diodes 9 may be controlled on the main body 3.

The invention claimed is:

1. A mouthpiece comprising:
a light irradiation section for irradiating front surfaces of teeth with light having a predetermined wavelength;
wherein said light irradiation section has a blue light emitting diode for emitting blue light to irradiate the teeth, said light irradiation section being operable to emit light at a blinking rate having a frequency in a range of greater than 1 kHz and no greater than 20 kHz.

2. The mouthpiece of claim 1, further comprising:
a horseshoe-shaped main body to be attached to an oral cavity; and
a belt like flexible substrate embedded in said main body, said light irradiation section being attached to said flexible substrate.

3. The mouthpiece of claim 2, wherein said flexible substrate is embedded in said main body so as to face the front surfaces of the teeth when said main body is attached to the oral cavity, said light irradiating section including a plurality of light emitting diodes arranged along a longitudinal direction of said flexible substrate so as to be operable to irradiate the entirety of the front surfaces of the teeth with the blue light.

4. The mouthpiece of claim 2, wherein said light irradiation section is operable to be set to a selected one of a plurality of irradiation times.

5. The mouthpiece of claim 4, further comprising a controller having a switch for setting said light irradiation section at the selected one of the irradiation times.

6. The mouthpiece of claim 5, wherein said controller is connected to said light irradiation section by an electronic cable.

7. The mouthpiece of claim 1, further comprising a controller having a switch for setting said light irradiation section at a selected one of a plurality of irradiation times.

8. The mouthpiece of claim 7, wherein said controller is connected to said light irradiation section by an electronic cable.

9. A mouthpiece comprising:
a light irradiation section for irradiating front surfaces of teeth with light having a predetermined wavelength;
wherein said light irradiation section has an ultraviolet light emitting diode for emitting ultraviolet light to irradiate the teeth, said light irradiation section being operable to emit light at a blinking rate having a frequency in a range of greater than 1 kHz and no greater than 20 kHz.

10. The mouthpiece of claim 9, further comprising:
a horseshoe-shaped main body to be attached to an oral cavity; and
a belt like flexible substrate embedded in said main body, said light irradiation section being attached to said flexible substrate.

11. The mouthpiece of claim 10, wherein said flexible substrate is embedded in said main body so as to face the front surfaces of the teeth when said main body is attached to the oral cavity, said light irradiating section including a plurality of light emitting diodes arranged along a longitudinal direction of said flexible substrate so as to be operable to irradiate the entirety of the front surfaces of the teeth with the ultraviolet light.

12. The mouthpiece of claim 10, wherein said light irradiation section is operable to be set to a selected one of a plurality of irradiation times.

13. The mouthpiece of claim 12, further comprising a controller having a switch for setting said light irradiation section at the selected one of the irradiation times.

14. The mouthpiece of claim 13, wherein said controller is connected to said light irradiation section by an electronic cable.

15. The mouthpiece of claim 9, further comprising a controller having a switch for setting said light irradiation section at a selected one of a plurality of irradiation times.

16. The mouthpiece of claim 15, wherein said controller is connected to said light irradiation section by an electronic cable.

* * * * *